(12) United States Patent
Doubler et al.

(10) Patent No.: US 7,033,399 B2
(45) Date of Patent: Apr. 25, 2006

(54) WELDED HIP PROSTHESIS

(75) Inventors: Robert L. Doubler, Ida, MI (US); John E. Hammill, Rossford, OH (US)

(73) Assignee: Ortho Innovations, Inc., Toledo, OH (US)

( * ) Notice: Subject to any disclaimer, the term of this patent is extended or adjusted under 35 U.S.C. 154(b) by 34 days.

(21) Appl. No.: 10/647,873

(22) Filed: Aug. 22, 2003

(65) Prior Publication Data

(51) Int. Cl.
*A61F 2/32* (2006.01)
(52) U.S. Cl. .................................................. 623/22.42
(58) Field of Classification Search .............. 623/22.42, 623/22.41, 23.15, 20.15, 20.29, 20.27, 23.18
See application file for complete search history.

(56) References Cited

U.S. PATENT DOCUMENTS

| | | | |
|---|---|---|---|
| 2,682,265 A | 6/1954 | Collison |
| 2,785,673 A | 3/1957 | Anderson |
| 3,067,740 A | 12/1962 | Haboush |
| 3,102,536 A | 9/1963 | Rose et al. |
| 3,806,957 A | 4/1974 | Shersher |
| 3,820,167 A | 6/1974 | Sivash |
| 3,848,272 A | 11/1974 | Noiles |
| 3,894,297 A | 7/1975 | Mittelmeier et al. |
| RE28,895 E | 7/1976 | Noiles |
| 3,987,499 A | 10/1976 | Scharbach et al. |
| 4,003,095 A | 1/1977 | Gristina |
| 4,004,300 A | 1/1977 | English |
| 4,021,865 A | 5/1977 | Charnley |
| 4,051,559 A | 10/1977 | Pifferi |
| 4,065,817 A | 1/1978 | Branemark et al. |
| 4,141,088 A | 2/1979 | Treace et al. |
| 4,167,047 A | 9/1979 | Grundei et al. |
| 4,404,691 A | 9/1983 | Bunning et al. |
| 4,419,026 A | 12/1983 | Leto |
| 4,549,319 A | 10/1985 | Meyer |
| 4,550,448 A | 11/1985 | Kenna |
| 4,687,486 A | 8/1987 | Brinckmann et al. |
| 4,728,333 A | 3/1988 | Masse et al. |
| 4,790,852 A | 12/1988 | Noiles |
| 4,808,186 A | 2/1989 | Smith |
| 4,846,839 A | 7/1989 | Noiles |
| 4,851,007 A | 7/1989 | Gray |
| 4,878,917 A | 11/1989 | Kranz et al. |
| 4,919,678 A | 4/1990 | Kranz |
| 4,938,774 A | 7/1990 | Tepic |
| 4,963,155 A | 10/1990 | Lazzeri et al. |
| 4,997,444 A | 3/1991 | Farling |
| 5,002,578 A | 3/1991 | Luman |
| 5,002,581 A | 3/1991 | Paxson et al. |
| 5,026,399 A | 6/1991 | Engelbrecht et al. |

(Continued)

FOREIGN PATENT DOCUMENTS

EP 0 567 349 10/1993

(Continued)

*Primary Examiner*—Alvin J. Stewart
(74) *Attorney, Agent, or Firm*—McHale & Slavin PA

(57) ABSTRACT

A hip prosthesis has a neck, a trochanter, a link, and an intramedullary rod. The intramedullary rod and the link are formed as a sub-assembly connected together endwise by a universal joint formed as a tubular extension. The link is telescoped into the trochanter and the neck, successively. A bolt is threaded into a threaded bore in one end of the link and draws the intramedullary rod and link into the trochanter resulting in an immovable press fit.

6 Claims, 4 Drawing Sheets

U.S. PATENT DOCUMENTS

| | | |
|---|---|---|
| 5,030,238 A | 7/1991 | Nieder et al. |
| 5,062,851 A | 11/1991 | Branemark |
| 5,080,685 A | 1/1992 | Bolesky et al. |
| 5,142,324 A | 8/1992 | Ito |
| 5,181,928 A | 1/1993 | Bolesky et al. |
| 5,281,260 A | 1/1994 | Kumar et al. |
| 5,286,260 A | 2/1994 | Bolesky et al. |
| 5,370,706 A | 12/1994 | Bolesky et al. |
| 5,397,360 A | 3/1995 | Cohen et al. |
| 5,441,537 A | 8/1995 | Kenna |
| 5,507,817 A | 4/1996 | Craig et al. |
| 5,507,829 A | 4/1996 | Thongpreda et al. |
| 5,509,935 A | 4/1996 | Fosco et al. |
| 5,540,694 A | 7/1996 | DeCarlo, Jr. et al. |
| 5,549,702 A | 8/1996 | Ries et al. |
| 5,653,765 A | 8/1997 | McTighe et al. |
| 5,702,480 A | 12/1997 | Kropf et al. |
| 5,725,592 A | 3/1998 | White et al. |
| 5,755,810 A | 5/1998 | Cunningham |
| 5,876,459 A | 3/1999 | Powell |
| 5,902,340 A * | 5/1999 | White et al. .............. 128/898 |
| 5,906,644 A | 5/1999 | Powell |
| 6,162,255 A * | 12/2000 | Oyola .................... 623/20.34 |
| 6,238,436 B1 * | 5/2001 | Lob et al. ............... 623/22.42 |
| 6,264,699 B1 * | 7/2001 | Noiles et al. ........... 623/23.23 |
| 6,299,648 B1 * | 10/2001 | Doubler et al. ......... 623/23.18 |
| 6,319,286 B1 * | 11/2001 | Fernandez et al. ...... 623/23.18 |
| 6,355,068 B1 * | 3/2002 | Doubler et al. ......... 623/22.42 |
| 6,428,578 B1 * | 8/2002 | White ..................... 623/23.22 |
| 6,440,171 B1 | 8/2002 | Doubler et al. |
| 6,692,530 B1 * | 2/2004 | Doubler et al. ......... 623/22.42 |
| 2002/0040244 A1 * | 4/2002 | Despres et al. ......... 623/22.15 |
| 2002/0120343 A1 * | 8/2002 | Doubler et al. ......... 623/22.42 |
| 2003/0074078 A1 * | 4/2003 | Doubler et al. ......... 623/22.42 |
| 2003/0149487 A1 | 8/2003 | Doubler et al. |

FOREIGN PATENT DOCUMENTS

| | | |
|---|---|---|
| EP | 0 729 732 | 9/1996 |
| EP | 0 970 665 | 1/2000 |
| WO | WO 96/01086 | 1/1996 |
| WO | WO 96/15736 | 5/1996 |

* cited by examiner

WELDED HIP PROSTHESIS

This application is related to an application entitled, Split Sleeve Modular Joint, Ser. No. 09/982,448, by the same inventors.

FIELD OF THE INVENTION

This invention relates to the medical field of orthopaedics and joint replacement, in particular. Modular artificial joints have several components that must be assembled and placed in the patient to reconstruct a joint. While modular joints provide the ability to custom fit an artificial joint to a patient's anatomy, the connection between the components must be without relative movement after implantation. This invention is directed to a modular artificial joint construction which provides a locking mechanism to secure the components immovably together.

BACKGROUND OF THE INVENTION

Artificial joints or prosthesis have now been constructed for almost every natural joint in the living body. As the medical field gains more understanding of the problems involved in mating inanimate constructions with animate tissue and designing mechanical devices that can duplicate natural movement, the number of implantations will continue to increase. In addition to the major joints, such as the hip, knee, shoulder, elbow, wrist and ankle, better engineering of the prosthesis, accompanied with miniaturization, will permit smaller and smaller natural joints, eg. vertebrae, phalanges, tarsals and metatarsals, to be reconstructed. Until now, the larger joints have received the most attention mainly because of the larger size of the bones. The prosthesis of this invention may be utilized in all joints.

In replacing a hip joint, the head of the femur is removed along with the ball. The trochanter portion of the femur is shaped and prepared for receiving the prosthesis so that the artificial joint will closely approximate the natural hip.

Earlier artificial hip joints were made of one-piece construction requiring a large inventory of prosthesis to accommodate the various sized patients. The modular artificial joint has two or three or more elements which replace the natural hip. By manufacturing these components with interchangeable connections but different external sizes, inventories may be smaller because of the ability to mix and match components. Also, the modular prosthesis provides more flexibility in customizing the various components of a joint to the various parts of a patient's natural joint.

In a three piece artificial hip joint, the various sized components of the joint that may be selected are the intramedullary rod, the trochanter and the neck. The intramedullary rod is inserted into the end of the femur. The rod acts as a stabilizer in maintaining the artificial joint in the axis of the femur. The upper portion of the rod which extends out of the femur is fitted into a trochanter element which is shaped like the removed broad head of the femur which it replaces. This element, along with the rod, is used to adjust the length of the prosthesis to approximate the natural length of the femur.

The natural trochanter is the broadened area offset from the end of the femur. The natural trochanter may be at any radial angle about the axis of the femur. This natural angular relationship must be reproduced by the intramedullary rod and the artificial trochanter. The artificial trochanter is seated on the end of the patient's femur and is the main load bearing element of the prosthesis. It is important that this load, which is mostly compression, is transmitted along the axis of the femur.

A neck element is inserted into the trochanter element and carries an extension onto which the ball joint will be fixed. The horizontal angle between the trochanter and the neck extension is variable to reproduce the anteversion angle of the patient's natural joint. The neck carries cantilevered forces in torque and compression between the acetabulum and the trochanter. It is also important that these forces do not result in relative movement between the trochanter and the neck.

All these elements have a central bore and are permanently secured together by a bolt which is inserted into the neck element, extends through the trochanter element, and is threaded into the upper end of the rod. In some cases, the intramedullary rod may be attached to the bone with bone cement while, in other cases the cement is omitted.

When the cement is omitted, the placement and fixation of the intramedullary rod becomes more critical to pain free usage of the prosthesis. Further, it is most important that the intramedullary rod not be disturbed after insertion since this would corrupt the union between the rod and the interior of the femur.

In order to maintain the original union between the femur and the intramedullary rod, modular prosthesis have been developed to allow rotational adjustment of the several parts or elements about the emplaced rod during the placement of the prosthesis to more closely reproduce the natural structure of the hip. It has been found that, in some cases, as the intramedullary rod has been inserted into the bone canal, there is rotational movement of the rod. In order to preserve the union between the rod and the bone, there must be a mechanism to accommodate the changed angular orientation of the proximal end of the intramedullary rod so that the prosthesis closely approximates the natural trochanter and ball.

While the above description refers to a modular hip prosthesis, substantially the same considerations must be given to other modular prosthesis, such as a knee prosthesis in which an intramedullary rod is placed in the lower end of the femur and in the upper end of the tibia or the elbow in which an intramedullary rod is placed in the lower end of the humerus and the upper end of the radius or ulna. Because of individual physical anomalies, the functional prosthesis must be capable of angular adjustment to conform to the natural physique.

With the advantage of flexibility gained by modular prosthesis, there comes the requirement that there be no movement between the several parts or elements after implantation. These movements may cause misalignment of the joint resulting in increased pain, trauma to the joint and, even, dislocation of the joint.

DESCRIPTION OF THE PRIOR ART

The prior art is replete with artificial prosthesis and hip joints, in particular.

Illustrative of the state of the art is U.S. Pat. No. 5,876,459 to Powell which discloses a modular hip joint having a stem, one end of which is inserted in the intramedullary canal. The other end of the stem is tapered to fit within a second, neck, element. The neck ultimately supports the ball joint. A sleeve element is placed over the junction of the first two elements. All three elements are rotationally movable relative to each other. A bolt is driven through the bore of the neck and stem deforming a portion of the interconnected elements for a friction fit between the neck and the stem. These prior art patents disclose that the sleeve may have a polygonal shaped bore with the articulating elements having corresponding shaped portions. The interconnected elements of these hip joints do not form a static lock between each other but require a deformation of one or more elements before a friction fit is established. The deformation and friction fit is between the stem and the neck rather than the sleeve and the stem.

U.S. Pat. No. 5,653,765, to McTighe et al discloses a modular hip joint with a stem, an intermediate shoulder portion, and a proximal shoulder piece which attaches to the ball. The stem and the intermediate shoulder portion have interengaging teeth on the corresponding ends of each by which they are connected. This end-to-end connection allows for rotational movement of the elements relative to each other. The proximal shoulder piece and the intermediate shoulder piece also have an end-to-end toothed connection for rotational adjustment. This construction has two movable end-to-end connections which provide good flexibility for rotation of the elements but have small surface areas of fixation to each other limited to the surfaces of the interengaged teeth.

The Leto patent, U.S. Pat. No. 4,419,026 issued Dec. 6, 1983, discloses a resilient split sleeve camming lock for use with telescoping tubular elements. The system relies on the resilience of the split ring and does not require a permanent deformation of the split sleeve by longitudinal displacement.

White et al, U.S. Pat. No. 5,725,592, disclose a three piece hip prosthesis with an artificial trochanter, intramedullary rod, and a neck for supporting the ball. The components are connected by complementary tapers.

U.S. Pat. No. 5,702,480, of Kropf et al, also have similar components.

SUMMARY OF THE INVENTION

In the instant invention a modular prosthesis is taught which has an intramedullary rod element which is to be inserted in a bone. The rod is a sub-assembly which includes a tapered extension allowing a movable connection between the proximal end of the rod and an elongated link. The proximal end of the intramedullary rod is permanently connected to the tapered tubular extension. The tapered extension is telescoped into one end of a bore in the artificial trochanter of the hip prosthesis. The mating surfaces of the extension and the weight-bearing trochanter bore are shaped to permit 360° rotation of the extension within the bore. The tapered wall shapes of the extension on the rod and the bore are complementary. This mechanism allows the trochanter to be rotated on the tapered tubular extension of the intramedullary rod without disturbing the placement of the rod in the intramedullary canal.

The internal wall of the tapered tubular extension is also tapered as is the external wall of the link. The proximal end of the link has an internally threaded bore for accepting a bolt.

Upon relative longitudinal movement between the trochanter bore and the tapered tubular extension a rotationally immovable connection is formed between the intramedullary rod and the weight-bearing element.

The artificial ball element is telescoped into the other end of the trochanter bore permitting additional rotational adjustment. All the elements are locked together by a bolt through the neck. As the bolt is tightened, the head engages the neck and the bolt draws the link upwards resulting in the tapered tubular extension to be wedged between the external taper of the link and the internal taper of the trochanter bore.

In one embodiment, the weight-bearing component has a narrow distal end and a larger proximal end forming an external shape approximating the natural bone. The weight-bearing component has a through bore from the distal end to the proximal end, with the proximal end of the through bore having a smooth circumference. The proximal end of the link is formed with opposite planar sides connected by curved walls. The distal end of the through bore has a circumference with opposite planar sides joined by curved surfaces. The circumference of the trochanter bore and the circumference of the proximal end of the link telescope together with the opposite planar surfaces in intimate contact with each other forming a rotationally secure connection with the artificial trochanter approximating the position of the natural trochanter.

The ball element has a planar distal end with a through bore. There is a cylindrical extension about the through bore adapted to be inserted into the proximal end of the through bore of the artificial trochanter. The extension and the wall of the trochanter bore may have complimentary shapes to interlock without rotational movement. Alternatively, there may be a key lock formed as a pin fitting into an aperture on the opposing contacting surfaces of the ball element and the trochanter. The proximal end of the through bore in the neck has an enlarged countersunk bore and the distal end of the through bore telescopes over the tapered tubular extension of the intramedullary rod. A screw threaded bolt is disposed in the countersunk bore and threadably engaged with the screw threads in the proximal end of the link forming a locked integral prosthesis.

Accordingly, it is an objective of the instant invention to provide a joint with an intramedullary rod sub-assembly which is connected with the weight-bearing element in such a manner as to provide infinite rotational adjustment therebetween. Rotational movement, in this context, refers to the turning of either element in a plane normal to the common longitudinal axis of both elements.

It is an objective of the instant invention to provide a sub-assembly of an intramedullary rod and a link movably connected together by a tapered tubular extension permanently fixed to the intramedullary rod.

It is another objective of the instant invention to provide a locking mechanism between the intramedullary rod and the weight-bearing element to permanently fix the components together after rotational adjustment.

It is a further objective of the instant invention to provide the trochanter and the neck with a locking mechanism to rigidly secure the components together to prevent relative rotation.

It is a still further objective of the invention provide a locking mechanism between the neck element and the trochanter element that permits rotational adjustment of the anteversion angle.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE INVENTION

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings.

Figure 1:
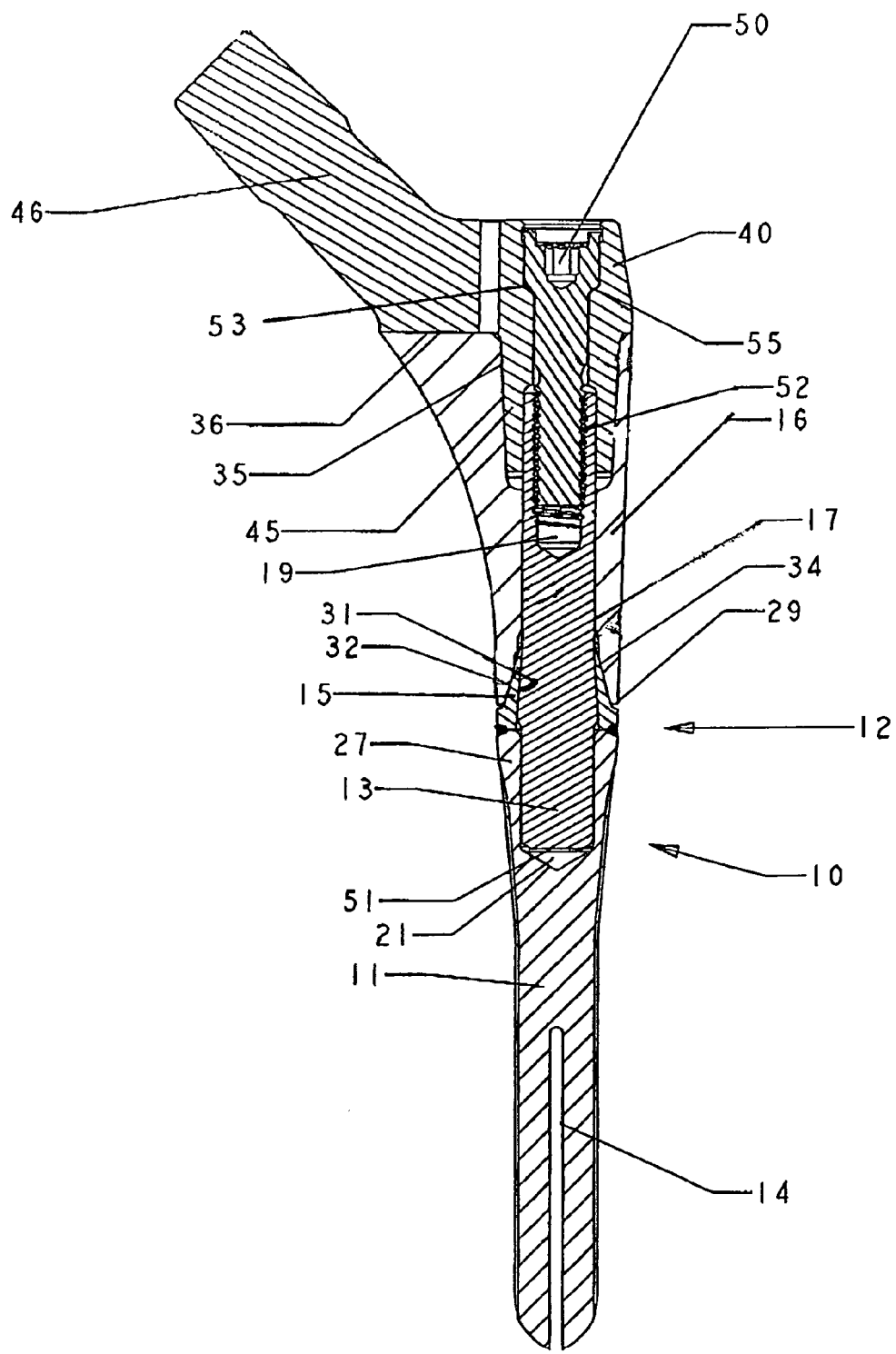
FIG. 1 is a cross section of the prosthesis of this invention.

The prosthesis 10, shown in FIG. 1, has an intramedullary rod 11 which provides stability. The distal end is inserted into the patient's femur and forms the stabilizing connection for maintaining the prosthesis in alignment with the axis of the femur. The distal end of the rod may have flutes to increase the surface area of the junction between the rod and the intramedullary canal of the femur. The distal end of the rod may also have a slot(s) 14 along the longitudinal axis of the rod to better accommodate the internal anomalies occurring in the interior of the intramedullary canal. This structure allows the distal end of the rod to compress to a smaller diameter to more easily reach the desired depth of insertion. Further, to accommodate the anatomy, the intramedullary rod may have an arcuate shape.

The link 13 and the intramedullary rod 11 are a pre-assembly 12 with a tapered tubular extension 15 forming a joint between the link 13 and the rod 11. These pre-assembled components of the prosthesis may be made in different sizes and provided as part of a kit to accommodate different sized patients.

The link 13 is formed in a columnar shape with a threaded bore 19 in one end and a bell shaped enlargement 29 near the other end. The end portion 51 of the link below the enlargement 29 is inserted in a blind bore 21 in the proximal end 27 of the intramedullary rod 11. The relative sizes of the blind bore and the end portion are such that the rod and link can move rotationally and longitudinally. The mouth of the tapered tubular extension 15 is placed over the end of the link 13 that has the threaded bore 19 with the larger diameter of the taper towards the enlargement. The tubular extension is slid down the link to contact the proximal end 27 of the intramedullary rod 11. The base 43 of the tapered tubular extension and the proximal end 27 of the intramedullary rod are permanently affixed about their respective circumferences. Depending on the materials used in the intramedullary rod and the tapered tubular extension, the seam 42 may be formed by a weld, such as by laser, causing autologous bonding or with additional flux or solvents, or adhesives. The connection of the rod and the extension leaves the link 13 a freely movable component.

Figure 2:
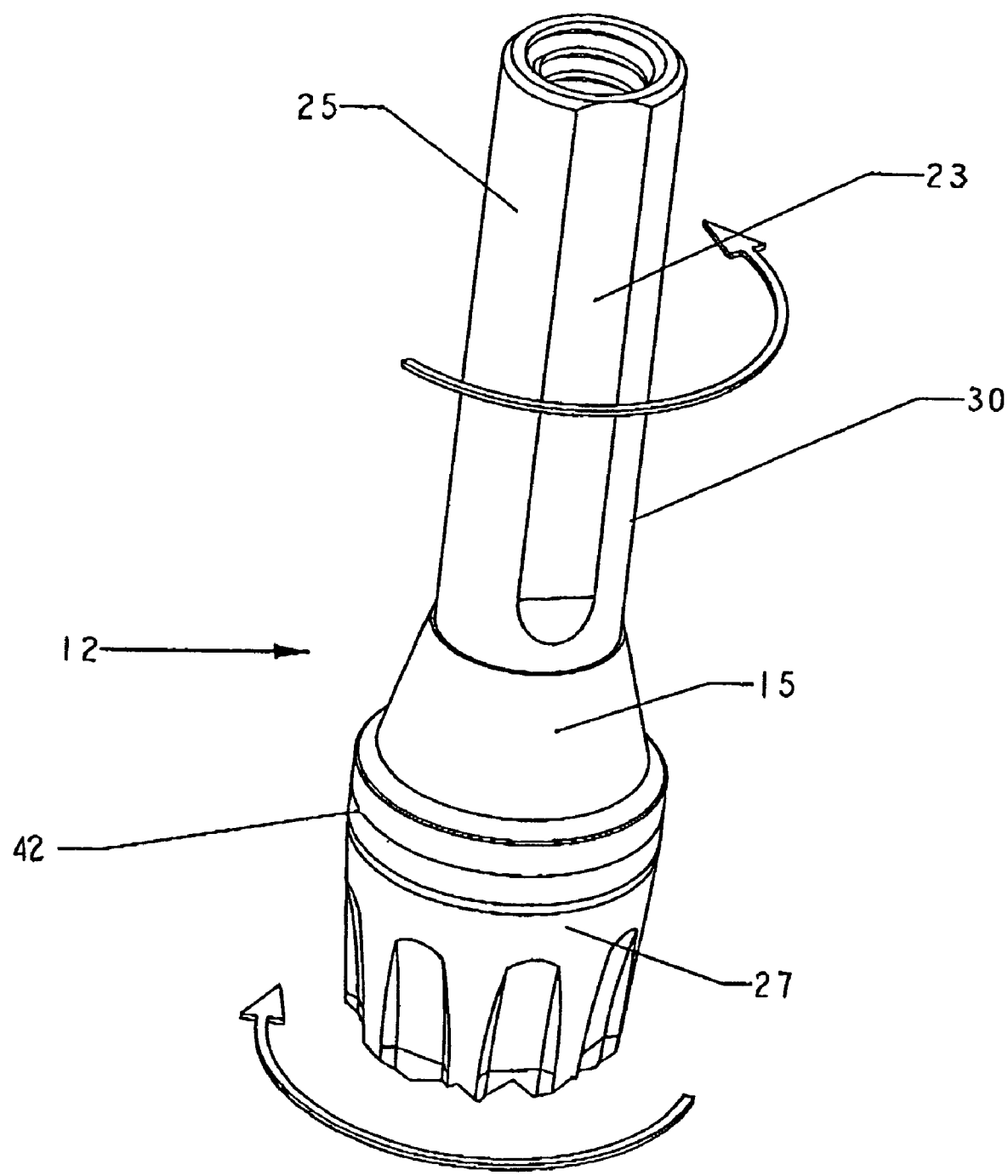
FIG. 2 shows a prospective view of the sub-assembly of the intramedullary rod and link.
Figure 3:
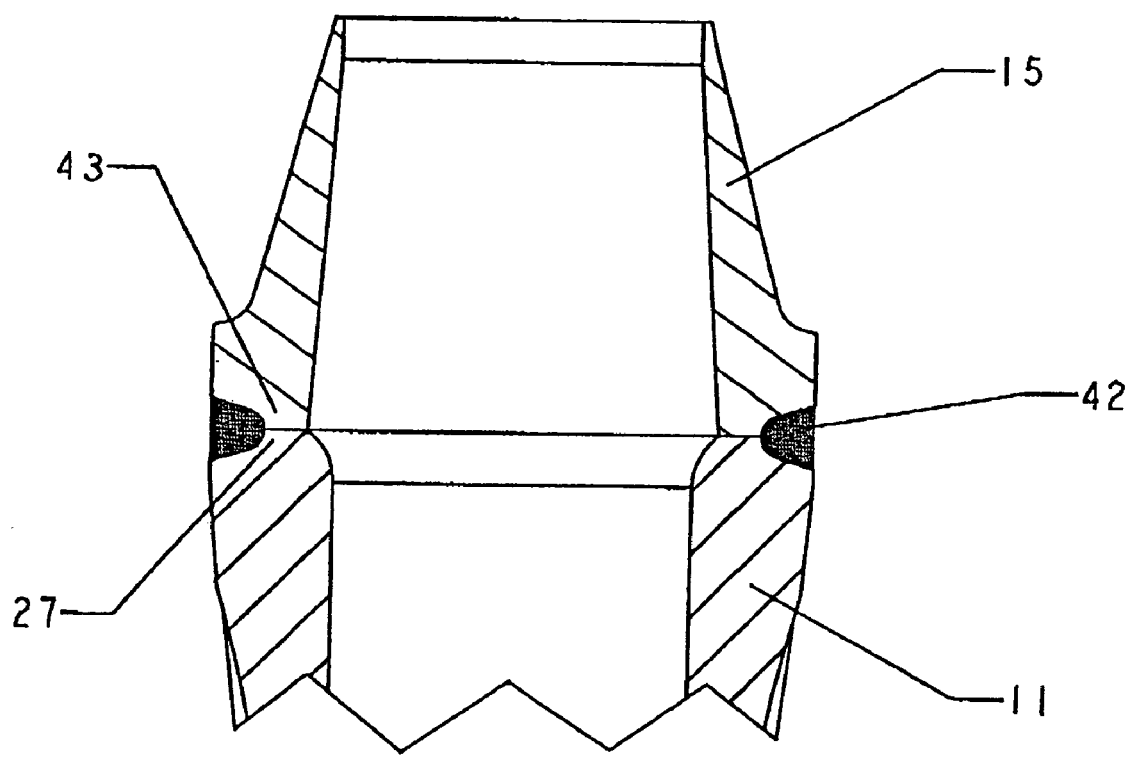
FIG. 3 is a cross section of the intramedullary rod and the tubular extension.
Figure 4:
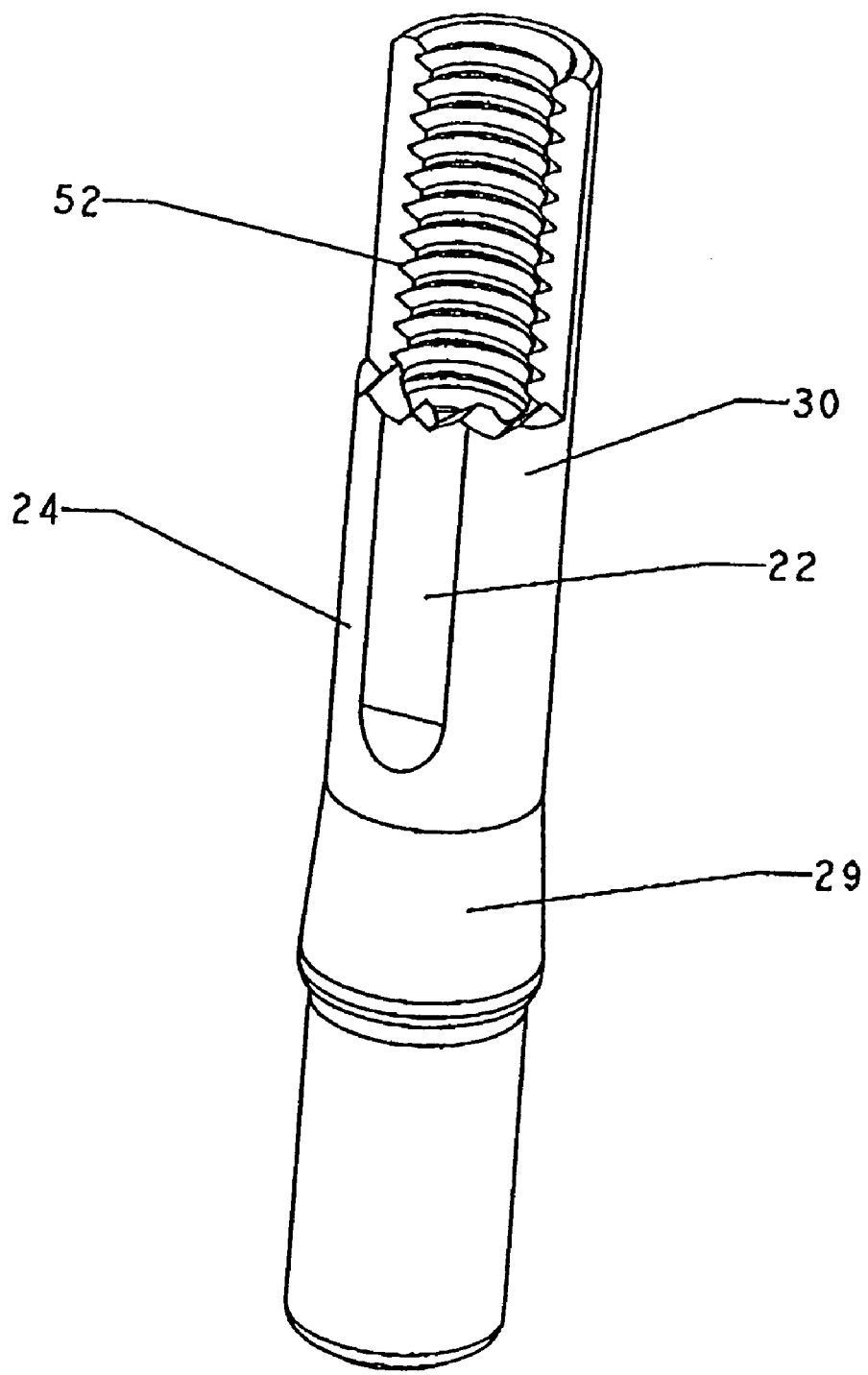
FIG. 4 shows a side view, partially in section, of the link used in this invention.

The trochanter element 16 is mounted on the tapered tubular extension 15. The trochanter has a through bore portion 17. In which the extension 15 is inserted. As shown in FIG. 2, the proximal end 30 of the link 13 has corresponding mating surfaces which lock the elements together preventing any rotational movement. The bore portion 17 has planar opposite sides and curved surfaces joining the ends of the planar sides. The proximal end of the link is sized to closely fit within the shaped bore portion 17. The proximal end of the link also has opposite planar sides 22 and 23 joined by curved surfaces 24 and 25.

In FIG. 1, the link 13 and the intramedullary rod 11 are shown fixed by the tapered tubular extension 15. The tubular extension may be deformable or resilient and may be made from the same bio-compatible materials as the remainder of the prosthesis. Before the extension is fixed in position, the intramedullary rod and the link may, each, be rotated freely about their longitudinal axis. This allows infinite angular adjustment of the link which, in turn, orients the angle of the trochanter without stress on the connection between the distal end of the rod and the intramedullary canal. Then the inner wall 31 of the tapered tubular extension 15 is pressed onto the outer surface of the bell shaped enlargement 29. The outer wall 32 is pressed against the inner surface of a bore 17.

As mentioned earlier, these components may be provided in different lengths and diameters. The proper insertion of the link allows the immovable connection of the trochanter to the intramedullary rod in the approximate original position of the excised head of the femur.

The distal end of the bore 17 in the trochanter has a taper 34 complementary with the exterior taper 32 of the tapered tubular extension 15.

The cooperating tapers 32 and 34 establish a precise limit to the distance the trochanter may be telescoped over the link. This limit, in turn, establishes the overall length of the two elements.

The link 13 has a blind bore 19 with internal threads 52 in the upper portion for receiving the threaded end of bolt 50 securing the neck 40 to the trochanter 16.

The bolt 50 cooperates with blind bore 18 in the distal end of the link to longitudinally translate the link as the threads 51 of the bolt are rotated within threads 52 and the head 53 of the bolt engages the counterbore 55 in the neck. As the bolt is rotated by an implement (not shown), the exterior taper of the tapered tubular extension 15 is press fit between the taper 34 of the distal end of the trochanter bore 17 and the internal wall is press fit with the enlargement 29 on the link. While a bolt is shown and described, other mechanical devices may be used to pull or push the link, the intramedullary rod, and the trochanter into a immovable press fit. Therefore, the more the bolt is tightened, the more compression is applied to the press fit. Ultimately, all three components are rigidly connected to each other. As shown and described, the link is telescoped into the proximal end of the intramedullary rod, obviously the telescoped components could be reversed.

The proximal end of trochanter 16 has a counter bore portion 35 which has a greater diameter than the diameter of the through bore portion 17 in the distal end. Counter bore portion 35 receives the distal end 45 of the neck element 40. This counter bore portion 35 may be cylindrical or conical. If conical, the walls of the counter bore portion 35 taper from a large diameter proximal end toward the distal end.

The counter bore portion 35 establishes a rotationally adjustable connection with the neck 40. This telescoped connection permits the prosthesis to be adjusted, after the intramedullary rod has been inserted into the femur, to approximate the natural location of the original ball.

The trochanter 16 is shaped like the natural femur head and has an outer diameter that is larger than the intramedullary rod at the distal end. The distal end of the trochanter is also inserted into the intramedullary canal. This junction of the trochanter and the shaft of the femur is the primary load carrying connection between the prosthesis and the patient's body. The trochanter flares to a larger diameter proximal end which has a planar surface 36 containing the counter bore portion 35. The bore 35 may include a linear portion forming a recess. The recess or bore extension may receive the tang of the key lock, such as shown and described in U.S. patent application Ser. No. 09/982,448, to establish the anteversion angle between the trochanter and the neck. The bore extension may be formed as an extension of the counter bore 35, however the recess may be separated from the bore.

The neck 40 has a partially cylindrical body with a laterally extending arm 46 extending from the proximal surface of the body. This arm 46 carries the ball joint (not shown) for an artificial hip and can be specifically set at different anteversion angles to the trochanter and thus the axis of the femur with the key lock.

The distal end 45 is telescoped into the counter bore portion 35 of the trochanter. The outer surface of the distal end may be cylindrical or conical. A conical surface of the distal end tapers from a smaller distal end toward the proximal surface. The base of the conical pin is complementary sized with the through bore portion 35 so that a friction fit is established when the elements are telescoped together. This maintains the rotational axis relationship between the elements.

The proximal end of the bore 19 is countersunk to receive the head of the bolt 50.

The prosthesis may be assembled without compromising the union between the intramedullary canal and the intramedullary rod. After the distal end of the rod is seated in the canal, the proximal end of the link is placed in the trochanter. The proximal end of the link can then be freely rotated to orient the shaped surfaces of the link and trochanter resulting in angular fixation of the position upon longitudinal translation.

Once the neck and trochanter are properly placed, The bolt is turned to engage the end of the threaded blind bore in link. Upon continued turning the proximal end of the link is longitudinally translated in relation to the intramedullary rod. Since the rod is fixed in the intramedullary canal, this causes the tapered tubular extension to engage both the distal end of the trochanter and the bell shaped enlargement in ever increasing pressure. By turning the threads of the bolt 50 into the threads 52 of the link these cooperating screw threads tighten and the elements of the prosthesis are drawn together forcing the tapered distal end of the neck into a friction fit with the tapered bore of the trochanter and the trochanter to a stop limit with the intramedullary rod sub-assembly. In the final disposition, the trochanter and the link are locked together over a major part of the length of each. And the neck is locked to the rotationally immovable trochanter at a specific anteversion angle.

The various elements or components of the prosthesis may be made in different external sizes so that a range of elements is available to meet the size needs of various patients. However, the interconnecting portions of the different sized components are of the same size or, at least, made in a range of sizes so that the different external sized elements may be securely connected as described above.

We claim:

1. A modular joint prosthesis comprising a neck, a trochanter, and a connected sub-assembly including an intramedullary rod, a fastener and a link, said link, and said intramedullary rod each freely and independently movable relative to one another subsequent said link and said rod being completely attached with each other and the modular joint prosthesis is secured to the patient's intramedullary canal, said neck having a through bore, said trochanter having a through bore, said intramedullary rod having a bore, said fastener welded to said intramedullary rod about said bore, said link extending through said fastener, said link adapted to be telescoped with said through bore of said trochanter and said through bore of said neck whereby said trochanter is between said intramedullary rod and said neck and said fastener is adapted to lock said trochanter and said sub-assembly together.

2. A modular joint of claim 1 wherein said fastner includes a tubular extension affixed to said intramedullary rod and encircles said link, said link and said tubular extension relatively movable.

3. A modular joint of claim 1 wherein said through bore in said trochanter is tapered and said tubular extension includes a complementary taper whereby said complementary tapers combine to form a press fit.

4. A modular joint of claim 1 wherein said link has planar surfaces and said through bore of said trochanter has complementary surfaces whereby said link and said trochanter are adapted be non-rotationally connected.

5. An artificial hip joint comprising a neck having a longitudinal axis with an arm for receiving a ball extending at an angle from said longitudinal axis, a through bore with a counter bore portion along said longitudinal axis, said through bore being countersunk, a trochanter with a through bore, a portion of said trochanter through bore adapted to receive said counter bore portion for rotational movement, an end portion of said trochanter through bore being tapered, and an integrally formed sub-assembly having a link and a intramedullary rod connected by a tubular extension, said tubular extension permanently attached to said intramedullary rod, said link and intramedullary rod being relatively independently movable, said link including a threaded bore, said link adapted for insertion in said countersunk through bore and said trochanter through bore, said tubular extension having a taper complementary with said tapered end portion of said trochanter through bore.

6. In a modular prosthesis to be used in bone joint replacement having a weight bearing component with a proximal end, a distal end, and a through bore therebetween, an intramedullary rod having a distal end and a proximal end, said proximal end including a bore adapted to be connected to said weight bearing component, the improvement comprising a sub-assembly composed of an elongated link having a proximal end and a distal end, said proximal end of said link including a tubular portion having a mouth, said distal end of said link being tapered toward said mouth, a tubular extension on said proximal end of said intramedullary rod, said tubular extension having an internal taper, said distal end of said link independently movably disposed within said bore in said proximal end of said intramedullary rod permitting relative rotational and longitudinal movement between said tubular extension and said link, said tubular extension rigidly affixed to said proximal end of said intramedullary rod, said improvement comprising said tubular extension being deformable to engage said link.

* * * * *